US009878480B1

(12) United States Patent
Grimes et al.

(10) Patent No.: US 9,878,480 B1
(45) Date of Patent: Jan. 30, 2018

(54) METHOD FOR MAKING POLYMER FEEDSTOCK USABLE FOR GENERATION OF FIBER HAVING ANTI-MICROBIAL PROPERTIES

(71) Applicant: PurThread Technologies, Inc., Cary, NC (US)

(72) Inventors: Lisa Thomas Grimes, Cary, NC (US); David John Reed, Charlotte, NC (US); Martin Wade Beasley, Cary, NC (US); Alan Fenner Boyd, Durham, NC (US); Lloyd Walter Frick, Chapel Hill, NC (US)

(73) Assignee: PurThread Technologies, Inc., Cary, NC (US)

( * ) Notice: Subject to any disclaimer, the term of this patent is extended or adjusted under 35 U.S.C. 154(b) by 329 days.

(21) Appl. No.: 14/748,761

(22) Filed: Jun. 24, 2015

Related U.S. Application Data

(60) Provisional application No. 62/016,634, filed on Jun. 24, 2014, provisional application No. 62/043,535, filed on Aug. 29, 2014, provisional application No. 62/049,691, filed on Sep. 12, 2014, provisional application No. 62/049,721, filed on Sep. 12, 2014.

(51) Int. Cl.
| | |
|---|---|
| *B29B 9/16* | (2006.01) |
| *B29B 13/04* | (2006.01) |
| *B29B 13/10* | (2006.01) |
| *C08J 3/22* | (2006.01) |
| *D01D 1/04* | (2006.01) |
| *D01D 5/08* | (2006.01) |
| *D01D 5/26* | (2006.01) |
| *D01F 1/02* | (2006.01) |
| *D01F 1/06* | (2006.01) |
| *D01F 1/07* | (2006.01) |
| *D01F 1/10* | (2006.01) |
| *B29C 47/00* | (2006.01) |
| *C08J 3/20* | (2006.01) |
| *B29C 47/88* | (2006.01) |
| *B29B 9/06* | (2006.01) |
| *B29K 67/00* | (2006.01) |
| *B29K 105/00* | (2006.01) |

(52) U.S. Cl.
CPC .......... *B29C 47/0066* (2013.01); *B29B 9/065* (2013.01); *B29B 13/045* (2013.01); *B29C 47/0004* (2013.01); *B29C 47/0016* (2013.01); *B29C 47/8805* (2013.01); *B29C 47/8815* (2013.01); *C08J 3/203* (2013.01); *C08J 3/226* (2013.01); *D01F 1/103* (2013.01); *B29K 2067/006* (2013.01); *B29K 2105/0011* (2013.01); *C08J 2367/03* (2013.01)

(58) Field of Classification Search
CPC ........... B29B 9/06; B29B 9/065; B29B 13/04; B29B 13/045; B29B 13/10; C08J 3/22; C08J 3/226; D01D 1/04; D01D 5/08; D01D 5/26; D01F 1/02; D01F 1/06; D01F 1/07; D01F 1/10; D01F 1/103
USPC ....... 264/78, 140, 143, 148, 210.6, 211, 237
See application file for complete search history.

(56) References Cited

U.S. PATENT DOCUMENTS

| | | | |
|---|---|---|---|
| 4,578,414 | A | 3/1986 | Sawyer et al. |
| 4,786,556 | A | 11/1988 | Hu et al. |
| 4,891,391 | A | 1/1990 | McEntee |
| 5,064,599 | A | 11/1991 | Ando et al. |
| 5,405,644 | A | 4/1995 | Ohsumi et al. |
| 6,192,965 | B1 | 2/2001 | Hinds |
| 6,384,168 | B1 | 5/2002 | Tanaka et al. |
| 6,394,168 | B1 | 5/2002 | Zoboski |
| 6,474,396 | B1 | 11/2002 | Toder |
| 6,723,428 | B1 | 4/2004 | Foss et al. |
| 6,841,244 | B2 | 1/2005 | Foss et al. |

(Continued)

FOREIGN PATENT DOCUMENTS

| | | |
|---|---|---|
| CN | 101705527 A | 5/2010 |
| EP | 2655709 A2 | 10/2013 |

(Continued)

OTHER PUBLICATIONS

"International Preliminary Report on Patentability" under Chapter 1 of the Patent Cooperation Treaty, in International Application No. PCT/US2014/050666, dated Feb. 16, 2016 (7 pages).
Sigma-Aldrich, MSDS for Copper (II) phthalocyanine, reprinted Feb. 7, 2013 (6 pages).
Czarnobaj, K. "Sol-gel-processed silica/polydimethylsiloxane/calcium xerogels as polymeric matrices for Metronidazole delivery system." Polym. Bull. 66:223-237 (2011) (15 pages).
"International Search Report" and "Written Opinion" of PCT Application No. PCT/US2014/050666, dated Jan. 22, 2015 (10 pages).

(Continued)

*Primary Examiner* — Leo B Tentoni
(74) *Attorney, Agent, or Firm* — Tillman Wright, PLLC; David R. Higgins; Neal B. Wolgin

(57) ABSTRACT

A method of making synthetic polymer pellet feedstock having a high concentration of an anti-microbial agent includes the steps of: introducing a polymer into a mixing vessel; introducing a polysiloxane dispersant into the mixing vessel; introducing an anti-microbial agent comprised of a powdered metal material into the mixing vessel; heating and mixing the polymer, the polysiloxane dispersant and the anti-microbial agent to form a molten blend that exhibits a generally homogenous dispersal of the anti-microbial agent; extruding the molten blend to form filaments; and cutting the filaments to form metalized synthetic polymer pellet feedstock. The powdered metal material includes particles of silver in metallic or salt form measuring between about 2 micrometers and about 12 micrometers and particles of copper in metallic or salt form measuring between about 2 micrometers and about 12 micrometers.

20 Claims, 8 Drawing Sheets

(56) References Cited

U.S. PATENT DOCUMENTS

| | | |
|---|---|---|
| 6,946,196 B2 | 9/2005 | Foss |
| 8,183,167 B1 | 5/2012 | Delattre et al. |
| 8,193,267 B2 | 6/2012 | Burton et al. |
| 2003/0204916 A1 | 11/2003 | Green et al. |
| 2004/0018359 A1 | 1/2004 | Haggquist |
| 2004/0096654 A1 | 5/2004 | Morin et al. |
| 2004/0180200 A1 | 9/2004 | Bertamini et al. |
| 2004/0259973 A1* | 12/2004 | Sakuma ................ D01F 1/103 523/122 |
| 2005/0028563 A1 | 2/2005 | Mullins et al. |
| 2005/0054830 A1 | 3/2005 | Islam et al. |
| 2005/0245685 A1* | 11/2005 | Otake ..................... C08J 3/22 525/191 |
| 2006/0074154 A1 | 4/2006 | Harashina et al. |
| 2006/0142438 A1* | 6/2006 | Ishii ..................... C08L 67/02 524/100 |
| 2006/0246149 A1 | 11/2006 | Buchholz et al. |
| 2006/0252326 A1 | 11/2006 | Mishler |
| 2007/0261803 A1 | 11/2007 | Alexander et al. |
| 2008/0009586 A1 | 1/2008 | VanSumeren et al. |
| 2008/0063679 A1 | 3/2008 | Sawafta et al. |
| 2008/0090945 A1* | 4/2008 | Langrick ................ D01F 1/06 524/94 |
| 2008/0187603 A1 | 8/2008 | Sawafta |
| 2008/0197528 A1* | 8/2008 | Wood ..................... B29B 9/06 264/143 |
| 2008/0242794 A1 | 10/2008 | Sandford et al. |
| 2008/0268011 A1 | 10/2008 | Goldmann et al. |
| 2008/0283202 A1 | 11/2008 | Serio, III et al. |
| 2008/0306181 A1 | 12/2008 | Garey et al. |
| 2009/0068283 A1 | 3/2009 | Sugiura et al. |
| 2009/0130161 A1 | 5/2009 | Sarangapani |
| 2009/0218266 A1 | 9/2009 | Sawafta et al. |
| 2009/0246258 A1 | 10/2009 | Shukla et al. |
| 2009/0269379 A1 | 10/2009 | Herbst |
| 2009/0312456 A1* | 12/2009 | Changping ............ C08J 3/226 523/128 |
| 2010/0124861 A1 | 5/2010 | Wendler et al. |
| 2010/0136073 A1 | 6/2010 | Preuss et al. |
| 2010/0267885 A1* | 10/2010 | Harimoto ............... C08L 83/04 524/500 |
| 2011/0142900 A1 | 6/2011 | Ohta et al. |
| 2012/0083750 A1 | 4/2012 | Sansoucy |
| 2012/0094120 A1 | 4/2012 | Foss et al. |
| 2012/0141723 A1 | 6/2012 | Chuah et al. |
| 2012/0164449 A1 | 6/2012 | Foss |
| 2012/0222826 A1 | 9/2012 | Foss et al. |
| 2013/0152737 A1 | 6/2013 | Chen et al. |
| 2013/0209386 A1* | 8/2013 | Cove ...................... A61K 8/19 424/65 |
| 2014/0259721 A1* | 9/2014 | Durdag .................. F26B 5/16 34/95 |
| 2014/0374941 A1 | 12/2014 | Foss et al. |
| 2015/0044449 A1 | 2/2015 | Foss et al. |
| 2015/0147570 A1 | 5/2015 | Foss |
| 2015/0342990 A1 | 12/2015 | Baumann |
| 2017/0006860 A1 | 1/2017 | Foss et al. |
| 2017/0044691 A1 | 2/2017 | Foss |

FOREIGN PATENT DOCUMENTS

| | | |
|---|---|---|
| JP | 01-096244 A | 4/1989 |
| JP | 01-139805 A | 6/1989 |
| JP | H02-087004 U | 7/1990 |
| JP | 10-310935 A | 11/1998 |
| JP | 2001-011734 A | 1/2001 |
| JP | 2004-197242 A | 7/2004 |
| JP | 2009-108448 A | 5/2009 |
| KR | 10-0766418 B1 | 10/2007 |
| WO | 2000053413 A1 | 9/2000 |
| WO | 2007078076 A1 | 7/2007 |
| WO | 2008010199 A2 | 1/2008 |
| WO | 2010024423 A1 | 3/2010 |
| WO | 2012088507 A2 | 6/2012 |
| WO | 2012088507 A3 | 10/2012 |
| WO | 2015023644 A2 | 2/2015 |
| WO | 2015023644 A3 | 4/2015 |
| WO | 2015184347 A1 | 12/2015 |

OTHER PUBLICATIONS

"International Search Report" and "Written Opinion" of PCT Application No. PCT/US2011/067184, dated Aug. 24, 2012 (9 pages).
"European Search Report" for European Application No. 11850293.9, dated Apr. 16, 2014 (7 pages).

* cited by examiner

METHOD FOR MAKING POLYMER FEEDSTOCK USABLE FOR GENERATION OF FIBER HAVING ANTI-MICROBIAL PROPERTIES

CROSS REFERENCE TO RELATED APPLICATIONS

The present application is a U.S. non-provisional patent application of, and claims priority under 35 U.S.C. § 119(e) to, the following U.S. provisional patent applications:
(a) U.S. Patent Application Ser. No. 62/016,634, filed Jun. 24, 2014 and entitled, "FEEDSTOCK FOR POLYESTER YARN AND FIBER;"
(b) U.S. Patent Application Ser. No. 62/043,535, filed Aug. 29, 2014 and entitled, "FEEDSTOCK FOR SYNTHETIC POLYMER YARN AND FIBER;"
(c) U.S. Patent Application Ser. No. 62/049,691, filed Sep. 12, 2014 and entitled, "FEEDSTOCK FOR SYNTHETIC POLYMER YARN/FIBER AND MATERIALS MANUFACTURED THEREFROM;" and
(d) U.S. Patent Application Ser. No. 62/049,721, filed Sep. 12, 2014 and entitled, "FEEDSTOCK FOR SYNTHETIC POLYMER YARN/FIBER AND METHODS OF MAKING SAME."

The entirety of each of the foregoing U.S. provisional patent applications is incorporated herein by reference.

INCORPORATION BY REFERENCE OF RELATED APPLICATIONS

The entirety of each of the following commonly-owned U.S. patent applications and U.S. patent application publications is incorporated herein by reference:
(a) U.S. patent application Ser. No. 13/276,069, filed Oct. 18, 2011 and entitled, "ENHANCING AND PRESERVING ANTI-MICROBIAL PERFORMANCE IN FIBERS WITH PIGMENTS," which '069 application published as U.S. Patent Application Publication No. US 2012/0094120 A1 on Apr. 19, 2012;
(b) U.S. patent application Ser. No. 13/335,349, filed Dec. 22, 2011 and entitled, "FIBERS WITH IMPROVING ANTI-MICROBIAL PERFORMANCE," which '349 application published as U.S. Patent Application Publication No. US 2012/0164449 A1 on Jun. 28, 2012;
(c) U.S. patent application Ser. No. 13/454,583, filed Apr. 24, 2012 and entitled, "REPLACEABLE CURTAINS," which '583 application published as U.S. Patent Application Publication No. US 2012/0222826 A1 on Sep. 6, 2012; and
(d) U.S. patent application Ser. No. 14/457,546, filed Aug. 12, 2014 and entitled, "ANTIMICROBIAL AND ANTIFUNGAL POLYMER FIBERS, FABRICS, AND METHODS OF MANUFACTURE THEREOF," which '546 application published as U.S. Patent Application Publication No. US 2015/0044449 A1 on Feb. 12, 2015.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention generally relates to feedstock for synthetic polymer fibers, and, in particular, to feedstock pellets for synthetic polymer fibers that exhibit anti-microbial properties.

Background

Synthetic fibers such as polyester yarn and thread can be manufactured by melting polyester chips or pellets into a solution and then extruding the molten material through a spinneret. Extruded filaments are then formed into thread or yarn. It is possible to impart anti-microbial properties to such fibers using various known methods.

One such method for imparting anti-microbial properties to synthetic fibers involves coating the raw extruded filaments or completed fiber with different powders or solutions that contain an anti-microbial agent. Another known method involves dipping or coating completed garments or other articles made from such synthetic fibers with different powders or solutions that contain an anti-microbial agent.

Unfortunately, materials that are coated or dipped in accordance with these processes are generally ill-equipped to retain their anti-microbial properties for very long. Because the agent that imparts anti-microbial characteristics are merely affixed to the surface of the fiber or garment, the anti-microbial agent has a natural tendency to abrade or be washed away during laundering or even through normal wear and tear. As the anti-microbial efficacy of the underlying fiber or article dissipates, so does the useful lifespan of the fiber or article.

Adding an anti-microbial agent in a powder or particulate form to molten polymer allows the anti-microbial agent to thoroughly disperse in solution and bind to the polymer resin. Filaments or fibers made in this manner retain their anti-microbial characteristics much longer, and articles made from such filaments or fibers can generally be laundered and worn for much longer periods of time while maintaining their anti-microbial characteristics. Such a process is described, for example, in the aforementioned U.S. Patent Application Publication No. US 2012/0164449 A1 to Foss.

Specialized products such as polymer filaments that include anti-microbial agents are often manufactured in a batch process, which can make production scheduling a challenge. The process for manufacturing polymer pellets generally involves very large quantities of material, and often such manufacturing takes place in a continuous flow process that runs without interruption for days or weeks or longer. Manufacturers tend to prefer to make large quantities of such specialized polymers on an infrequent basis in order to minimize the process startup materials and waste. Large-scale production often yields large quantities of finished synthetic fiber that then need to be warehoused until needed for finished goods manufacturing. The result is higher manufacturing and storage costs.

As such, a need exists for an improved method of specialized synthetic fiber production capable of yielding smaller batches that can be tailored to suit a particular need. For example, a need exists for a method of smaller scale batch production of synthetic polymer fibers that have a particular desired concentration of anti-microbial agent. In addition to the foregoing, a need exists for a method of synthetic polymer fiber production that blends the constituent materials in a way that yields homogeneous dispersal of the anti-microbial agent throughout the resultant fibers. A need also exists for a method of producing synthetic polymer fibers that exhibit overall enhanced anti-microbial efficacy.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect includes a method of making synthetic polymer pellet feedstock having a high concentration of an anti-microbial agent. The method includes the steps of: introducing a polymer into a mixing vessel; introducing a polysiloxane dispersant into the mixing vessel; introducing an anti-microbial agent comprised of a powdered metal material into the mixing vessel; heating and mixing the polymer, the polysiloxane dispersant and the anti-microbial agent to form a molten blend that exhibits a generally homogenous dispersal of the anti-microbial agent; extruding the molten blend to form filaments; and cutting the filaments to form metalized synthetic polymer pellet feedstock. The polymer is selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6. The powdered metal material includes: particles of silver, in metallic or salt form, measuring between about 2 micrometers and about 12 micrometers; and particles of copper, in metallic or salt form, measuring between about 2 micrometers and about 12 micrometers.

In a feature of this aspect, the particles of silver may include particles of silver sulfate, and the particles of copper may include copper sulfate pentahydrate.

In another feature of this aspect, the particles of silver and the particles of copper may each measure between about 5 micrometers and about 8 micrometers.

In other features of this aspect, the polymer may include polyethylene terephthalate (PET); and/or the polymer may include polybutylene terephthalate (PBT).

In another feature of this aspect, the polymer may be in a powdered form. In another feature of this aspect, the polymer may be in a pellet form.

In another feature of this aspect, the polysiloxane dispersant may be introduced to the mixing vessel at different intervals separated by at least a mixing step.

In another feature of this aspect, the method may further include cooling the metalized synthetic polymer pellet feedstock by air-cooling. In another feature of this aspect, the method may further include cooling the metalized synthetic polymer pellet feedstock by water-cooling.

In another feature of this aspect, the method may further include levigating the powdered metal material. In another feature of this aspect, the powdered metal material may be levigated prior to introduction into the mixing vessel.

In another feature of this aspect, the method may further include a re-processing step that includes: introducing at least a portion of the metalized synthetic polymer pellet feedstock into the mixing vessel; heating and mixing the portion of the metalized synthetic polymer pellet feedstock to form a re-processed molten blend; extruding the re-processed molten blend to form filaments; and cutting the filaments to form re-processed metalized synthetic polymer pellet feedstock.

In another feature of this aspect, the re-processing step may further include: introducing a dye to the mixing vessel with the portion of the metalized synthetic polymer pellet feedstock; and mixing the dye and the portion of the metalized synthetic polymer pellet feedstock within the mixing vessel.

In another feature of this aspect, the re-processing step may further include: introducing an insecticide to the mixing vessel with the portion of the metalized synthetic polymer pellet feedstock; and mixing the insecticide and the portion of the metalized synthetic polymer pellet feedstock within the mixing vessel.

In another feature of this aspect, the re-processing step may further include: introducing a flame retardant to the mixing vessel with the portion of the metalized synthetic polymer pellet feedstock; and mixing the flame retardant and the portion of the metalized synthetic polymer pellet feedstock within the mixing vessel.

Broadly defined, the present invention according to another aspect includes a method of making synthetic polymer pellet feedstock having a high concentration of an anti-microbial agent. The method includes: introducing a polymer into a mixing vessel; introducing a polysiloxane dispersant into the mixing vessel; introducing an anti-microbial agent comprised of a powdered metal material; heating and mixing the polymer, the polysiloxane dispersant and the anti-microbial agent to form a molten blend that exhibits a generally homogenous dispersal of the anti-microbial agent; extruding the molten blend to form filaments; and cutting the filaments to form metalized synthetic polymer pellet feedstock. The powdered metal material that consists of: particles of silver in metallic or salt form; and particles of copper in metallic or salt form.

In a feature of this aspect, the particles of silver may include particles of silver sulfate, and the particles of copper may include copper sulfate pentahydrate.

In another feature of this aspect, the particles of silver sulfate and the particles of copper sulfate pentahydrate may each measure between about 2 micrometers and about 12 micrometers.

In another feature of this aspect, the particles of silver sulfate and the particles of copper sulfate pentahydrate may measure between about 5 micrometers and about 8 micrometers.

In another feature of this aspect, the polymer may be selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6. In other features of this aspect, the polymer may include polyethylene terephthalate (PET); and/or the polymer may include polybutylene terephthalate (PBT).

In another feature of this aspect, the polymer may be in a powdered form. In another feature of this aspect, the polymer may be in a pellet form.

In another feature of this aspect, the polysiloxane dispersant may be introduced to the mixing vessel at different intervals separated by at least a mixing step.

In another feature of this aspect, the method may further include cooling the metalized synthetic polymer pellet feedstock by air-cooling. In another feature of this aspect, the method may further include cooling the metalized synthetic polymer pellet feedstock by water-cooling.

In another feature of this aspect, the method may further include levigating the powdered metal material. In another feature of this aspect, the powdered metal material may be levigated prior to introduction into the mixing vessel.

In another feature of this aspect, the method may further include a re-processing step that includes: introducing at least a portion of the metalized synthetic polymer pellet feedstock into the mixing vessel; heating and mixing the portion of the metalized synthetic polymer pellet feedstock to form a re-processed molten blend; extruding the re-processed molten blend to form filaments; and cutting the filaments to form re-processed metalized synthetic polymer pellet feedstock.

In another feature of this aspect, the re-processing step may further include: introducing a dye to the mixing vessel with the portion of the metalized synthetic polymer pellet feedstock; and mixing the dye and the portion of the metalized synthetic polymer pellet feedstock within the mixing vessel.

In another feature of this aspect, the re-processing step may further include: introducing an insecticide to the mixing vessel with the portion of the metalized synthetic polymer pellet feedstock; and mixing the insecticide and the portion of the metalized synthetic polymer pellet feedstock within the mixing vessel.

In another feature of this aspect, the re-processing step may further include: introducing a flame retardant to the mixing vessel with the portion of the metalized synthetic polymer pellet feedstock; and mixing the flame retardant and the portion of the metalized synthetic polymer pellet feedstock within the mixing vessel.

In other features of this aspect, the weight percentage of the silver sulfate in the metalized synthetic polymer pellet feedstock may be about 23%; the weight percentage of the copper sulfate pentahydrate in the metalized synthetic polymer pellet feedstock may be about 5%; and/or the weight percentage of the polysiloxane dispersant in the metalized synthetic polymer pellet feedstock may be about 3%.

Broadly defined, the present invention according to another aspect includes a method of making an anti-microbial yarn or fiber. The method includes the step of making metalized synthetic polymer pellet feedstock by: introducing a first polymer into a first mixing vessel; introducing a dispersant into the first mixing vessel; introducing an anti-microbial agent comprised of a powdered metal material into the first mixing vessel; heating and mixing the polymer, the dispersant and the anti-microbial agent to form a first molten blend that exhibits a generally homogenous dispersal of the anti-microbial agent; extruding the first molten blend to form filaments; and cutting the filaments to form the metalized synthetic polymer pellet feedstock. The powdered metal material includes: particles of silver, in metallic or salt form, measuring between about 2 micrometers and about 12 micrometers; and particles of copper, in metallic or salt form, measuring between about 2 micrometers and about 12 micrometers. The method further includes the steps of: introducing at least a portion of the metalized synthetic polymer pellet feedstock into a second mixing vessel; introducing a second polymer into the second mixing vessel; heating and mixing the portion of the metalized synthetic polymer pellet feedstock and the second polymer to form a second molten blend; and extruding the second molten blend to form filaments usable to make an anti-microbial yarn or fiber.

In another feature of this aspect, the dispersant may include a polysiloxane.

In a feature of this aspect, the particles of silver may include particles of silver sulfate, and the particles of copper may include copper sulfate pentahydrate.

In another feature of this aspect, the particles of silver and the particles of copper may each measure between about 5 micrometers and about 8 micrometers.

In another feature of this aspect, the yarn or fiber may have a concentration of about 2520 ppm silver sulfate and about 318 ppm copper sulfate pentahydrate.

In another feature of this aspect, the first polymer may be selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6.

In another feature of this aspect, the first polymer may be in a powdered form. In another feature of this aspect, the first polymer may be in a pellet form.

In another feature of this aspect, the second polymer may be selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6.

In another feature of this aspect, the second polymer may be in a powdered form. In another feature of this aspect, the second polymer may be in a pellet form.

In another feature of this aspect, the method may further include levigating the powdered metal material. In another feature of this aspect, the powdered metal material may be levigated prior to introduction into the first mixing vessel.

In another feature of this aspect, the first polymer and the second polymer may be the same type of polymer. In another feature of this aspect, the first polymer and the second polymer may be different types of polymers.

Broadly defined, the present invention according to another aspect includes a synthetic polymer pellet feedstock having a high concentration of an anti-microbial agent. The synthetic polymer pellet feedstock includes: a polymer; a polysiloxane dispersant; and an anti-microbial agent comprised of a powdered metal material. The polymer is selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6. The powdered metal material includes: particles of silver, in metallic or salt form, measuring between about 2 micrometers and about 12 micrometers; and particles of copper, in metallic or salt form, measuring between about 2 micrometers and about 12 micrometers. The synthetic polymer pellet feedstock exhibits generally homogenous dispersal of the anti-microbial agent.

In a feature of this aspect, the particles of silver may include particles of silver sulfate, and the particles of copper may include copper sulfate pentahydrate.

In another feature of this aspect, the particles of silver and the particles of copper may each measure between about 5 micrometers and about 8 micrometers.

In other features of this aspect, the polymer may include polyethylene terephthalate (PET); and/or the polymer may include polybutylene terephthalate (PBT).

In other features of this aspect, the synthetic polymer pellet feedstock may further include a dye; the synthetic polymer pellet feedstock may further include an insecticide; and/or the synthetic polymer pellet feedstock may further include a flame retardant.

Broadly defined, the present invention according to another aspect includes a synthetic polymer pellet feedstock having a high concentration of an anti-microbial agent. The synthetic polymer pellet feedstock includes: a polymer; a polysiloxane dispersant; and an anti-microbial agent comprised of a powdered metal material. The powdered metal material consists of: particles of silver in metallic or salt form; and particles of copper in metallic or salt form. The synthetic polymer pellet feedstock exhibits generally homogenous dispersal of the anti-microbial agent.

In a feature of this aspect, the particles of silver may include particles of silver sulfate, and the particles of copper may include copper sulfate pentahydrate.

In another feature of this aspect, the particles of silver and the particles of copper may each measure between about 2 micrometers and about 12 micrometers.

In another feature of this aspect, the particles of silver and the particles of copper may each measure between about 5 micrometers and about 8 micrometers.

In another feature of this aspect, the polymer is selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6. In other features of this aspect, the polymer may include polyethylene terephthalate (PET); and/or the polymer may include polybutylene terephthalate (PBT).

In other features of this aspect, the synthetic polymer pellet feedstock may further include a dye; the synthetic polymer pellet feedstock may further include an insecticide; and/or the synthetic polymer pellet feedstock may further include a flame retardant.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
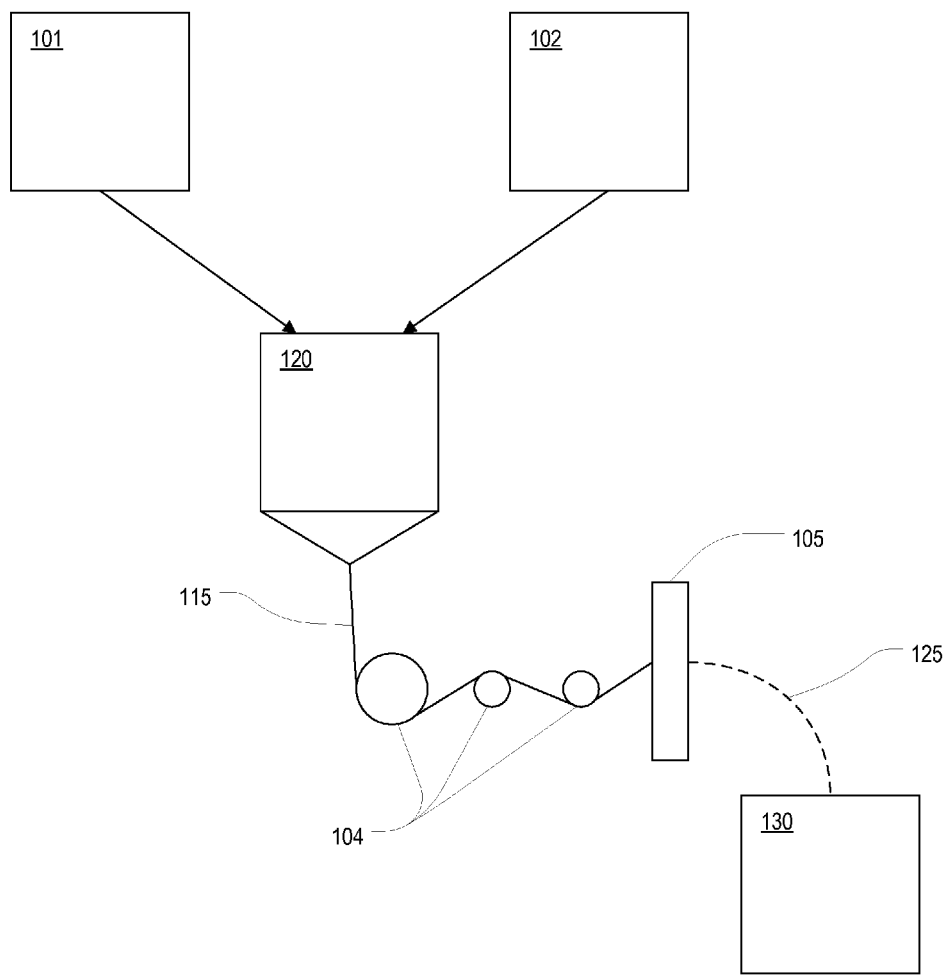
FIG. 1 is a schematic diagram illustrating a system and method for making synthetic polymer pellet feedstock.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

It is contemplated that the systems and methods described herein can be undertaken and/or applied using a wide variety of polymers and other synthetic materials that can be used alone or in combination with one another. In particular, it is contemplated that polymers and other synthetic materials for use in connection with the systems and methods of the present invention include, but are not limited to: thermoplastic polymers; polyester; nylon; nylon 6; nylon 6,6; rayon; polyethylene (PE); polypropylene (PP); polyethylene terephthalate (PET); polybutylene terephthalate (PBT); polyethylene terephthalate glycol (PETG); co-PET; polylactic acid (PLA); and polytrimethylene terephthalate (PTT).

FIG. 1 is a schematic diagram illustrating a system and method for making synthetic polymer pellet feedstock. With reference to FIG. 1, hoppers 101,102 store constituent materials for making a synthetic polymer fiber. Metered amounts of constituent materials from hoppers 101 and 102 are drawn into a polymerization reactor 120. Once polymerization occurs and the molten polymer has reached the correct temperature, molten polymer is then drawn from the polymerization reactor 120 as one or more filaments 115. The drawn filaments 115 are then stretched and cooled by passing through one or more rollers 104 or other means. Once the filaments 115 have reached the desired thickness and temperature, the filaments 115 are then pulled and/or otherwise guided through a cutter 105, where the filaments 115 are chopped into polymer pellets 125. Polymer pellets 125 are then stored in another hopper 130 for later use as feedstock for other processes that include, for example, making polymer pellet feedstock having a high concentration of an anti-microbial agent (also referred to herein as "super pellets" or "super pellet feedstock").

Figure 2:
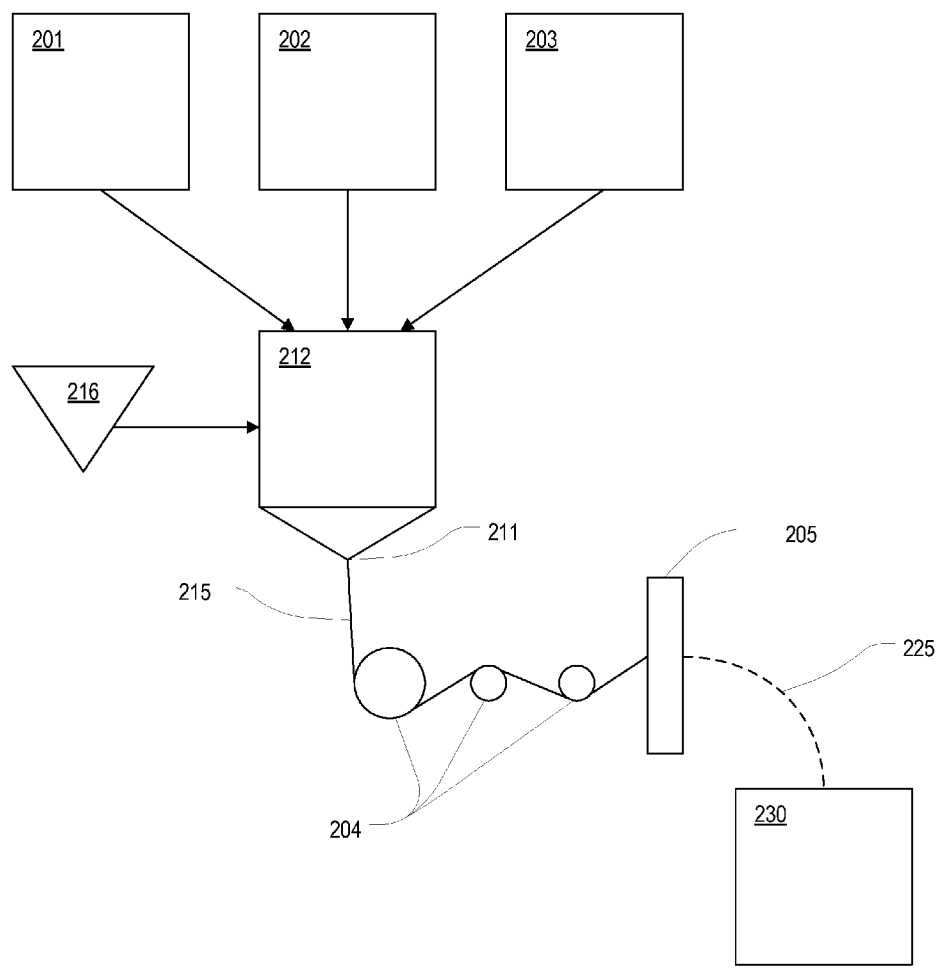
FIG. 2 is a schematic diagram illustrating a system and method for making synthetic polymer pellet feedstock having a high concentration of an anti-microbial agent in accordance with one or more aspects of the present invention.

FIG. 2 is a schematic diagram illustrating a system and method for making synthetic polymer pellet feedstock having a high concentration of an anti-microbial agent in accordance with one or more aspects of the present invention. With reference to FIG. 2, polymer pellet feedstock, such as the polymer pellets 125 from the storage hopper 130 discussed above in connection with FIG. 1, are stored in a hopper 201 and metered into a mixing vessel 212. Additional hoppers 202,203 store one or more anti-microbial agents that are metered into the mixing vessel in desired quantities. Though the system and method depicted in FIG. 2 contemplates different anti-microbial agents metered from different hoppers, a single anti-microbial agent metered from a single hopper is likewise contemplated. In contemplated embodiments, the one or more anti-microbial agents are in the form of powdered metals and/or metal salts that include, but are not limited to, copper, silver, zinc, and salts of any of the foregoing. Contemplated metal salts that may be used as anti-microbial agents include silver sulfate and copper sulfate. Other metals and metal salts are likewise contemplated as an anti-microbial agent for use in connection with the systems and methods of the present invention. Notably, the amount and type of powdered metals or metal salts can be selected to impart resulting super pellets with desirable properties, including enhanced durability and enhanced anti-microbial efficacy.

With further reference to FIG. 2, pellets metered from hopper 201 and powdered metals or metal salts metered from hoppers 202,203 are mixed with a dispersant material metered into the mixing vessel 212 from a storage vessel 216. In a contemplated embodiment, the dispersant includes a polysiloxane material, such as a silicone fluid. Polysiloxanes can have a dispersant effect that helps facilitate even distribution of the metal powders that are introduced into the mixing vessel as anti-microbial agents. One such polysiloxane capable of use in connection with the systems and methods of the present invention is XIAMETER® PMX-200 Silicone Fluid, 350CST, manufactured by Dow Corning Corporation of Midland, Mich. The pellets from the first hopper 201, the powdered metals or metals salts from the other hoppers 202,203, and the dispersant may be metered and mixed simultaneously or in a desired sequence. The dispersant, the polymer pellets, and the powdered metals or metal salts can be heated to a molten state and thoroughly mixed, for example by high shear mixing at a high speed.

It is contemplated that other materials may be applied in place of, or in addition to, the polysiloxane material in order to disperse or evenly distribute the metal powders within the blend. For example, various other chemicals, such as surfactants or wetting agents, can be used as dispersants.

Once the blend of materials has been heated and mixed, the molten blend can be extruded or otherwise drawn from the mixing vessel 212 via a spinneret 211 or the like as one or more filaments 215. The drawn filaments 215 are then stretched and cooled by passing through one or more rollers 204 or other means. Once the filaments 215 have reached the desired thickness and temperature, the filaments 215 are then pulled and/or otherwise guided through a cutter 205, where the filaments 215 are chopped into super pellets 225 that have a high concentration of one or more anti-microbial agents. The super pellets can then be stored in another hopper 230 for further processing. In a contemplated embodiment, the super pellets 225 are metalized super pellets.

In a particular contemplated embodiment, one hopper 202 of FIG. 2 stores a powdered silver salt, and another hopper 203 of FIG. 2 stores a powdered copper salt. Commercially available metal salt particles are ground and sieved, using techniques familiar to one skilled in the art to provide silver salt particles and copper salt particles of a desired size. It is contemplated that the silver salt particles in hopper 202 have a size distribution of about 2 micrometers to about 12 micrometers, with a maximum size of about 15 micrometers. In a preferred embodiment, the silver salt particles in hopper 202 have a size distribution of about 5 micrometers to about 8 micrometers. It is also contemplated that the copper salt particles in hopper 203 have a size distribution of about 2 micrometers to about 12 micrometers, with a maximum size of about 15 micrometers. In a preferred embodiment, the copper salt particles in hopper 203 have a size distribution of about 5 micrometers to about 8 micrometers. In at least some embodiments, the silver salt is a silver sulfate, and the copper salt is a dried copper sulfate (e.g., copper sulfate pentahydrate).

For both silver salt particles and copper salt particles, the selected particle size of about 2 micrometers to about 12 micrometers is particularly helpful in facilitating more comprehensive surface area coverage at the surface of the polymer, thereby enhancing anti-microbial activity. Furthermore, grinding the silver salt particles and copper salt particles to a size within the size distribution of about 2 to about 12 micrometers ensures that the silver salt particles and copper salt particles are able to pass through the extrusion equipment, including the spinneret 211, during the fiber generation process. As such, a method of fiber generation that utilizes silver salt particles and copper salt particles of generally uniform size within the size distribution of about 2 to about 12 micrometers is more efficient, as the blend of materials can be run or extruded more smoothly without causing an obstruction commonly attributed to larger particles.

Uniform particle size can also enhance anti-microbial activity. Silver salt particles and copper salt particles within the same size range disperse more evenly and consistently within the mixture. As a result, pathogens that encounter fibers made from super pellets that have been metalized with silver salt particles and copper salt particles of generally uniform size are exposed to the anti-microbial agent on a more uniform basis. In this regard, utilization of silver salt particles and copper salt particles of generally uniform size enhances homogeneity of the compound/blend, which yields enhanced anti-microbial activity in the resultant fibers or filaments.

Though the foregoing discussion includes utilization of both silver salt particles and copper salt particles as anti-microbial agents, it will further be appreciated that other forms of silver, copper and other elements may be utilized with or in place of silver salts, copper salts, or both. For example, it is contemplated that silver and copper particles in their metallic forms may be utilized with similar effect. Furthermore, other types of particles may be utilized, such as zinc in its metallic form or its salt form.

In at least some embodiments, the one or more anti-microbial agents, such as powdered metals or metal salts, are levigated prior to being introduced into hoppers 202,203 or prior to being metered into the mixing vessel 212. As referred to herein, levigation involves separately wetting each anti-microbial agent with a wetting agent or surfactant.

In a contemplated embodiment, the anti-microbial agents are levigated with an amount of the dispersant from storage vessel 316, such as a polysiloxane material. Once wetted, each anti-microbial agent may be formed into a wet paste that can be introduced into the hoppers 202,203 for metering into the mixing vessel 212. Alternatively, the anti-microbial agents can be levigated together within the mixing vessel 212.

Levigation facilitates improved mixing of the anti-microbial agent with the other ingredients within the mixing vessel 212 such that the resultant blend has a generally uniform concentration of anti-microbial particles and generally uniform viscosity. Fibers generated using a system or method that involves a levigation step can exhibit enhanced homogeneity, with anti-microbial particles more evenly dispersed throughout the fiber. Furthermore, resultant fibers exhibit generally uniform levels of anti-microbial activity and are generally free from weak regions having little to no anti-microbial activity.

With reference to embodiments that utilize one or more powdered metal materials as anti-microbial agents, levigation causes the powdered metal materials to form a wet paste that can be introduced into the hoppers 202,203 or directly into the mixing vessel 212. For example, it is contemplated that silver salt particles and copper salt particles may each be separately wetted via levigation prior to introduction into the hoppers 202,203 or the mixing vessel 212.

As discussed previously, a wide variety of different polymers can be used with the systems and methods of the present invention. In one contemplated embodiment, the polymer pellets are polyester pellets (such as polyethylene terephthalate (PET) or polybutylene terephthalate (PBT) pellets), which can enhance durability, wrinkle resistance and color retention of garments or other articles made using fibers generated with the polyester pellets. In another contemplated embodiment, the polymer pellets are nylon pellets (including nylon, nylon 6, or nylon 6,6). Materials based at least in part on nylon can exhibit anti-drip, slow burn properties.

Figure 3:
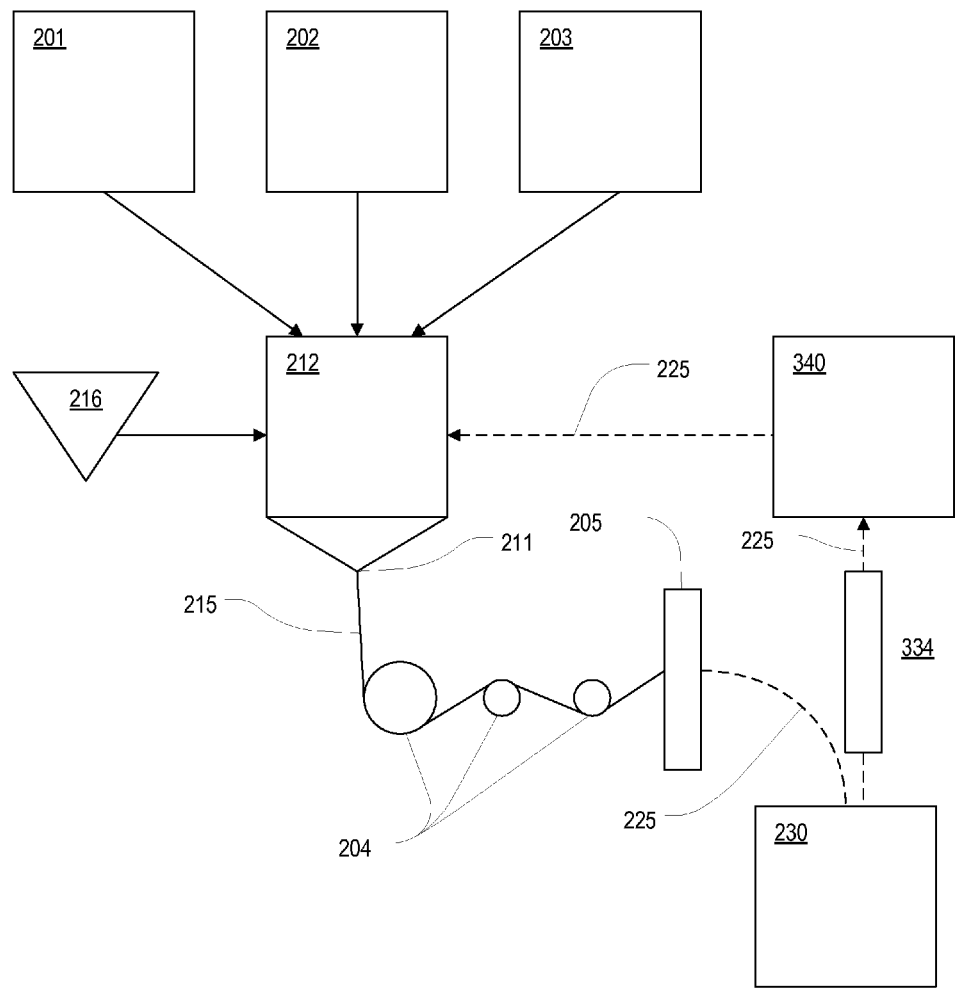
FIG. 3 is a schematic diagram illustrating another system and method for making synthetic polymer pellet feedstock having a high concentration of an anti-microbial agent in accordance with one or more aspects of the present invention, shown with an additional re-processing cycle.

FIG. 3 is a schematic diagram illustrating another system and method for making synthetic polymer pellet feedstock having a high concentration of an anti-microbial agent in accordance with one or more aspects of the present invention, shown with an additional re-processing cycle. The system and method of FIG. 3 proceeds generally as described above in connection with FIG. 2 to form super pellets 225. The super pellets 225 can then optionally be re-processed one or more times, as shown in FIG. 3. Formed super pellets 225 can be drawn from hopper 230 and delivered to hopper 340 by a conveying means 334 such as a conveyor belt or vacuum tube. The super pellets 225 can then be metered back into the mixing vessel 212 and heated until the super pellets 225 have melted.

In some embodiments, only the super pellets are heated and otherwise re-processed, while in other embodiments, additional dispersant materials or anti-microbial agents, such as powdered metals or metal salts, may be added during one of the re-processing steps in order to increase the concentration of the anti-microbial agent in the resultant super pellet feedstock or otherwise enhance or refine the super pellet feedstock. In some contemplated embodiments, the super pellets may be metered back into the mixing vessel 212 along with one or more additives (such as, for example, pigments, tints, dyes, or the like) to impart the super pellets with additional features, such as a particular desired color. In one such embodiment, the super pellets are re-processed with a carbon black dye. In other embodiments, the super pellets may be metered back into the mixing vessel 212 along with an insecticide (such as, for example, pyrethrin) and/or a flame retardant.

The molten blend can then be re-extruded through spinneret 211. The process then continues as before, with filaments 215 stretched and cooled by passing through one or more rollers 204 and then pulled through a cutter 205, where the filaments 215 are chopped into super pellets that have a high concentration of one or more anti-microbial agents.

In accordance with the embodiment depicted in FIG. 3, the extrusion, stretching, cooling, and chopping, may occur any number of times. In one or more preferred embodiments, the re-processing cycle occurs between four and seven times. Between re-processing cycles, it is contemplated that formed super pellets 225 can also be air-cooled or water-cooled (via a water bath). Re-processing of the super pellets results in super pellet feedstock that has superior anti-microbial properties including, but not limited to, enhanced durability and enhanced anti-microbial efficacy.

Figure 4:
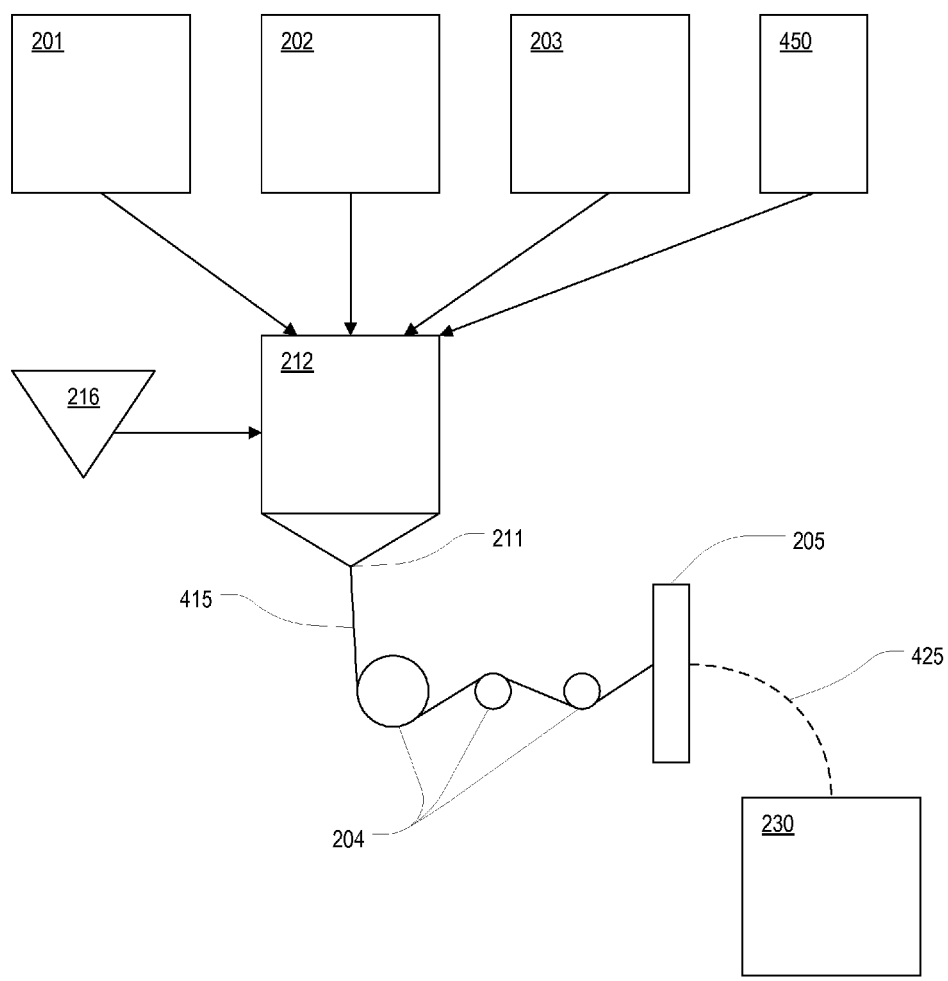
FIGS. 4 and 5 are schematic diagrams illustrating other systems and methods for making synthetic polymer pellet feedstock having a high concentration of an anti-microbial agent in accordance with one or more aspects of the present invention.
Figure 5:
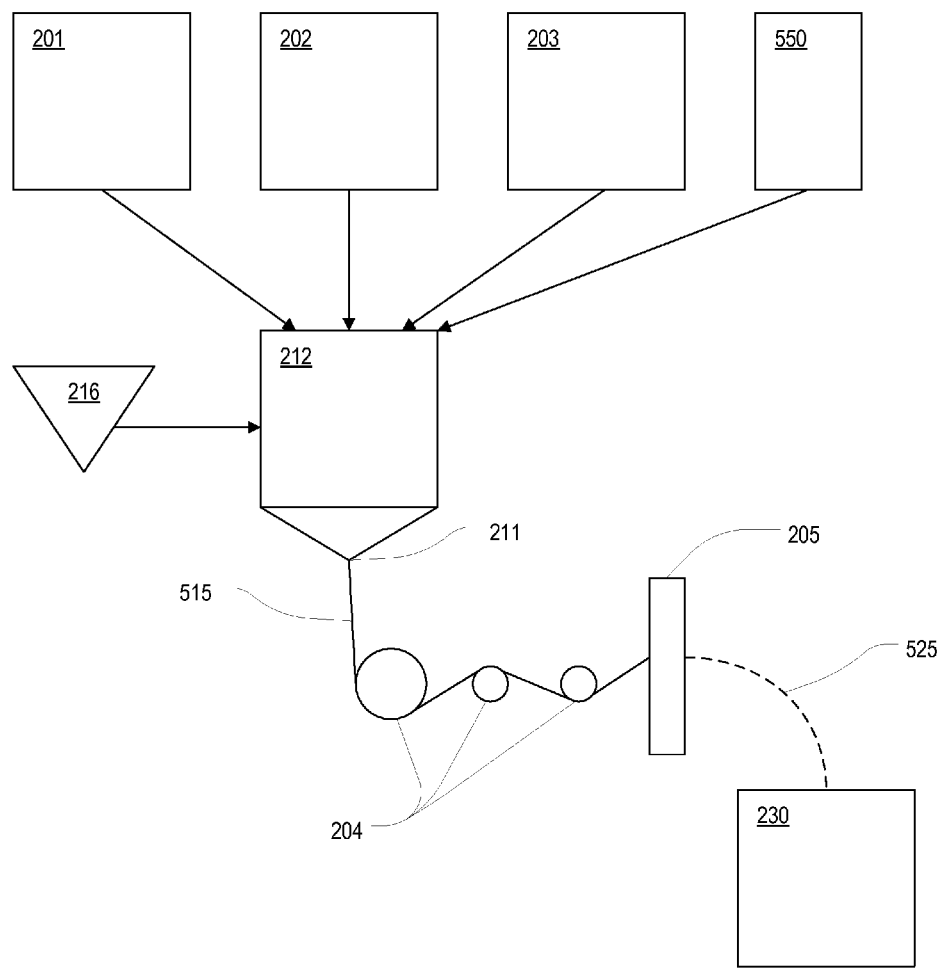

FIGS. 4 and 5 are schematic diagrams illustrating other systems and methods for making synthetic polymer pellet feedstock having a high concentration of an anti-microbial agent in accordance with one or more aspects of the present invention.

The system and method of FIG. 4 proceeds generally as described above in connection with FIG. 2; however, super pellet feedstock made in accordance with the system and method of FIG. 4 also includes one or more materials for imparting the pellets with insecticidal properties in addition to the afore-described anti-microbial properties. With reference to FIG. 4, a hopper 450 stores one or more materials, such as pyrethrin, that exhibit insecticidal properties. A desired amount of pyrethrin or other material(s) is metered from hopper 450 into the mixing vessel 212 to be mixed with synthetic polymer pellets, a dispersant material, and one or more anti-microbial agents, such as powdered metals or metal salts, as described above in connection with FIG. 2. Filaments 415 drawn from the molten mixture are extruded through spinneret 211. The process then continues in similar manner to that described above in connection with FIG. 2, with filaments 415 being stretched and cooled by passing through one or more rollers 204 and then being pulled and/or otherwise guided through a cutter 205, where the filaments 415 are chopped into super pellets 425 that have a high concentration of one or more anti-microbial agents and also exhibit insecticidal properties. Various end-use materials (such as textiles, garments, and the like) that are made using fibers derived from the super pellets 425 can exhibit insecticidal properties as well as the desired anti-microbial properties.

The system and method of FIG. 5 proceeds generally as described above in connection with FIG. 2; however, super pellet feedstock made in accordance with the system and method of FIG. 5 also includes one or more flame retardants for imparting the pellets with flame retardant properties in addition to the afore-described anti-microbial properties. With reference to FIG. 5, a hopper 550 stores one or more flame retardants. A desired amount of the flame retardant is metered from hopper 550 into the mixing vessel 212 to be mixed with synthetic polymer pellets, a dispersant material, and one or more anti-microbial agents, such as powdered metals or metal salts, as described above in connection with FIG. 2. Filaments 515 drawn from the molten mixture are extruded through spinneret 211. The process then continues in similar manner to that described above in connection with FIG. 2, with filaments 515 being stretched and cooled by passing through one or more rollers 204 and then being pulled and/or otherwise guided through a cutter 205, where the filaments 515 are chopped into super pellets 525 that have a high concentration of one or more anti-microbial agents and also exhibit flame retardant properties. Various end-use materials (such as textiles, garments, and the like) that are made using fibers derived from the super pellets 525 can exhibit flame retardant properties as well as the desired anti-microbial properties.

With reference to FIGS. 2-5, one reason for making super pellets relates to the batch nature of polymer-based manufacturing processes. Manufacture of super pellets allows for more flexibility in making specialized polymer fibers or pellets in a manufacturing process better suited to small batch production, as will be explained in greater detail below in connection with FIG. 6. Super pellets are also generally easy to store and transport and are less susceptible to damage while in transit and storage.

Figure 6:
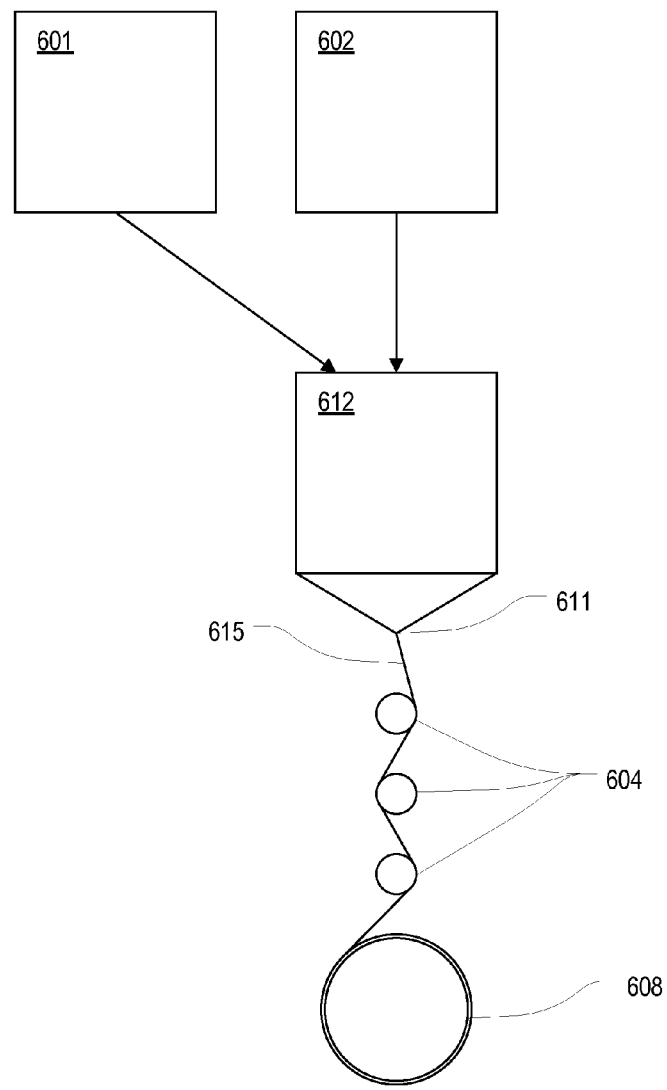
FIG. 6 is a schematic diagram illustrating a system and method for making synthetic polymer filament from plain synthetic polymer pellets and synthetic polymer pellet feedstock having a high concentration of an anti-microbial agent in accordance with one or more aspects of the present invention.

FIG. 6 is a schematic diagram illustrating a system and method for making synthetic polymer filament from plain synthetic polymer pellets and synthetic polymer pellet feedstock, in the form of super pellets having a high concentration of an anti-microbial agent, in accordance with one or more aspects of the present invention. As shown in FIG. 6, plain polymer pellets (such as polyester pellets, including, for example, polyethylene terephthalate (PET) pellets, or polybutylene terephthalate (PBT) pellets) are stored in hopper 601, and super pellets that include a high concentration of an anti-microbial agent are stored in hopper 602. Plain polymer pellets and super pellets are drawn from their respective hoppers in a desired ratio and mixed in a heated mixing vessel 612, where both types of pellets are melted into a molten state. The molten blend is drawn via a spinneret 611, thereby forming multiple polymer filaments 615. The polymer filaments 615 are further drawn and cooled by passing through a series of rollers 604. The polymer filaments 615 can then be wrapped around a drum 608 and stored as a finished intermediate product, which is then used to manufacture fiber, yarn, and similar products from which garments or other materials can then be made.

In a contemplated embodiment, the blend of molten polymer pellets in the mixing vessel 612 can further include a dispersant, such as a polysiloxane material, as discussed above in connection with FIGS. 2-5.

It is further contemplated that, instead of wrapping the polymer filaments 615 around a drum 608, filaments 615 can also be chopped into pellets again for further processing. For example, it is contemplated that pellets made using the system and method of FIG. 6 can be letdown with additional plain polymer pellets in order to further refine the concentration of anti-microbial agent within the extruded synthetic fibers.

As discussed previously, a wide variety of different polymers can be used with the systems and methods of the present invention. In particular, with respect to FIG. 6, a wide variety of different polymers can be used as either the plain polymer pellets or as an ingredient in the super pellets. In one contemplated embodiment, one or both of the plain polymer pellets and the super pellets include polybutylene terephthalate (PBT). In another contemplated embodiment, one or both of the plain polymer pellets and the super pellets include polyethylene terephthalate (PET).

By using super pellets in conjunction with plain polymer pellets, it is possible to manufacture a wide variety of filament products from a single production run of super pellets. By varying the ratio of super pellets to plain polymer pellets in the manufacturing process, a variety of finished filament products can be made on demand, each with a particular desired end concentration of the anti-microbial agent. Resulting filament products can therefore have a variety of anti-microbial properties. Since it is difficult to predict the specific type of anti-microbial properties that a fabric or garment manufacturer may desire, the ability to combine a small variety of polymer pellets to produce a wide variety of desired filaments has great appeal to garment and fabric manufacturers.

The systems and methods described herein are capable of use in conjunction with the manufacture of a wide variety of end-use products. As described above in connection with FIG. 6, end-use products made from synthetic fibers extruded from a blend of plain polymer pellets and super pellets can exhibit anti-microbial properties tailored to a particular purpose for which the product is intended to be used. Furthermore, products generated with such fibers can exhibit generally uniform anti-microbial efficacy based on the homogeneous dispersal of anti-microbial agent throughout the fibers. Still further, such products can exhibit improved durability following sustained use and improved efficacy against a wide variety of pathogens, including bacteria, fungi and viruses.

It is contemplated that synthetic fibers made in accordance with one or more systems and methods described herein can be implemented for use in the manufacture of products and materials that include, but are not limited to: (i) textiles or garments that include pyrethrin or other insecticidal substances; (ii) anti-thermal or anti-infrared (anti-IR) textiles, garments or blankets, which may, for example, be applied to soft or hard surfaces in order to obscure a surface from night-vision viewers; (iii) textiles or garments that include body armor-related materials, such as KEVLAR®, manufactured by the E. I. du Pont de Nemours and Company chemical company; (iv) thermo-chromographic textiles or garments, which exhibit the ability to change appearance or color when a user (e.g., patients at medical facilities, or military personnel) becomes overheated; (v) compression bandages or compression clothing or textiles, which can be used to decrease the proliferation of bacteria and other pathogens; (vi) liners for disposable diapers (adult or infant) or feminine pads; and (vii) liners of bandages where cotton is contained beneath the liner, which may be useful for bandages that include an antihemorrhagic agent to stop bleeding.

EXAMPLES

Example 1

In a contemplated embodiment, the constituent powdered metal salts and silicone include: (i) silver Sulfate AgFX 98.5% (Silver Fiber/Film Extrusion Antimicrobial Additive for Polyester and Polyolefin), Kodak, EPA No. 59441-8; (ii) copper Sulfate pentahydrate CUAM 100 99%, Kodak, EPA No. 59441-11 (material is dried/micronized); and Xiameter PMX-200 Silicone Fluid 350CS, Dow Corning.

Example 1 involves manufacture of a 200 lb pre-blend of super pellets, which is scaled up to a 500 lb master batch of PBT-based pellets. In the scaled-up batch, a ratio of 40% super pellets to 60% virgin PBT pellets is used. In another contemplated embodiment, the super pellets are scaled up using powdered PBT. In yet another contemplated embodiment, the ratio of super pellets to virgin PBT pellets is 25:75 instead of 40:60.

Manufacture is completed on Henschel HIM 350L production equipment.

Constituent materials of the pre-blend super pellets is set forth in Table 1A, below.

TABLE 1A

Constituent Materials of Example 1 (200 lb Pre-Blend Super Pellets)

| INGREDIENT | % w/w | lbs/200 lbs |
|---|---|---|
| silver sulfate | 22.75% w/w | 45.5 lbs |
| copper sulfate, dried | 5.0% w/w | 10.0 lbs |
| Xiameter PMX-200 Silicone Fluid, 350 CST | 2.8125% w/w | 5.625 lbs |
| polybutylene terephthalate (PBT) (powdered) | 69.4375% w/w | 138.875 lbs |

A contemplated order of mixing steps is: (1) charge dried, powdered PBT into Henschel HIM 350L high shear mixer; (2) charge silver sulfate AgFX into HIM 350L high shear mixer (9.1% of total batch weight of 500 lbs); (3) charge copper sulfate pentahydrate (dried/milled) into HIM 350L high shear mixer (2.0% of total batch weight of 500 lbs) [copper sulfate pentahydrate is weighed just before use very quickly in order to minimize moisture uptake in bulk container]; (4) begin high shear mixing and charge ½ of Xiameter PMX-200 Silicone Fluid 350CS (0.5625% of total batch weight of 500 lbs) onto ingredients spinning in high shear mixer; (5) blend at high speed for 1 minute; (6) stop blender and scrape down powders from walls and paddle into bulk powder bed; (7) begin high shear mixing and charge remaining ½ of Xiameter PMX-200 Silicone Fluid 350CS (0.5625% of total batch weight of 500 lbs) onto ingredients spinning in high shear mixer; (8) blend at high speed for 1 minute; (9) stop blender and scrape down powders from walls and paddle into bulk powder bed; and (10) blend at high speed for 1 minute.

Following the mixing process, the molten blend can be extruded and pelleted. In-process quality control tests can be performed on resultant super pellets as well as virgin PBT pellets. Quality control tests include: bulk density (~60 pellets/gram); bulk density per 100 mL; specific gravity (pycnometer); residual moisture content (weight loss balance); ash %; and TGA (thermogravimetric analysis). Pellets/materials can be sampled at beginning of run, middle of run, and end of run.

The pre-blend super pellets are scaled up to a 500 lb master batch in a 40:60 ratio of super pellets to virgin PBT pellets. Constituent materials of the 500 lb scaled up master batch are set forth in Table 1B, below.

TABLE 1B

Constituent Materials of Example 1 (500 lb Scale-Up)

| | INGREDIENT | % w/w | lbs/500 lbs |
|---|---|---|---|
| PRE-BLEND Super Pellets (40% w/w) | silver sulfate | 9.1% w/w | 45.5 lbs |
| | copper sulfate, dried | 2.0% w/w | 10.0 lbs |
| | Xiameter PMX-200 Silicone Fluid, 350 CST | 1.125% w/w | 5.625 lbs |
| | polybutylene terephthalate (PBT) (powdered) | 27.775% w/w | 138.876 lbs |
| Virgin PBT Pellets (60% w/w) | virgin polybutylene terephthalate (PBT) pellets | 60.0% w/w | 300.0 lbs |

Scaled up master batch pellets can be used to manufacture a wide variety of filament products from a single production run of super pellets. In one contemplated embodiment, the scaled up master batch pellets are letdown in polyethylene terephthalate (PET) at a 4% letdown ratio. Fibers manufactured from the 4% letdown in PET and garments knitted with 100% of such fibers can exhibit a target elemental concentration of about 0.364% w/w silver sulfate and about 0.08% w/w copper sulfate dried. Measured in parts per million, the target elemental concentration of such fibers (or resultant garments or other articles) is 2520 ppm silver sulfate and 318 ppm copper sulfate dried.

Example 2

In another contemplated embodiment, the constituent powdered metals include: (i) silver sulfate AgFX 98.5% (Silver Fiber/Film Extrusion Antimicrobial Additive for Polyester and Polyolefin) [Kodak, EPA No. 59441-8]; and (ii) copper sulfate pentahydrate [FibroChem, EPA No. 35896-0]. A silicone, such as a polysiloxane (at any selected viscosity), can also be selected as a constituent material. Constituent materials of this contemplated embodiment are also set forth in Table 2, below.

TABLE 2

| Constituent Materials of Example 2 | |
| --- | --- |
| silver sulfate | 13.68% w/w |
| copper sulfate, dried | 2.88% w/w |
| polybutylene terephthalate (PBT) | 83.44% w/w |

A contemplated sequential mixing order for the above constituent materials using a high shear mixer, is: (1) PBT and/or PET, (2) copper sulfate, and (3) silver sulfate.

Example 3

In another contemplated embodiment, the constituent materials used to create a super pellet include: (i) silver sulfate; (ii) copper sulfate, dried; (iii) Xiameter PMX-200 Silicone Fluid, 350CST1; and (iv) PBT and/or PET. Constituent materials of this contemplated embodiment are also set forth in Table 3, below.

TABLE 3

| Constituent Materials of Example 3 | |
| --- | --- |
| silver sulfate | 13.68% w/w |
| copper sulfate, dried | 2.88% w/w |
| Xiameter PMX-200 Silicone Fluid, 350 CST | 1.56% w/w |
| PBT or PET | 81.88% w/w |

A contemplated sequential mixing order for the above constituent materials using a high shear mixer, is: (1) PBT and/or PET, (2) silicone fluid, (3) copper sulfate, and (4) silver sulfate.

Example 4

Three master batches of super pellets (MB 1066, MB 1067 and MB 1068) were made in accordance with one or more aspects of the present invention. Hosiery legs were made from these master batches using textured filaments. MB 1066 and MB 1067 were generated using generally uniform particle size of the anti-microbial metal materials. MB 1068 was also generated using generally uniform particle size of the anti-microbial metal materials. Additionally, for MB 1068 the anti-microbial metal materials were levigated prior to introduction in the mixing vessel.

The samples were each washed in 1% Triton X-100, rinsed in hot tap water, and dried overnight. A Glo® assay was used. An overnight culture of $E.$ $coli$ was diluted 1:1 with fresh media and grown for an hour before being centrifuged and re-suspended in saline Triton X-100. Aliquots (10 µl) of $E.$ $coli$ in saline (0.9%) with Triton X-100 (0.1%) were added to tubes containing small pieces of fabric, tamped down, and incubated at room temperature. After one hour, 400 µl of BacTiter-Glo® reagent was added, and the luminescence of a 100-µl aliquot was measured in the luminometer. The "% remaining" was calculated by reference to the luminescence of an aliquot of the culture in saline Triton X-100. Samples of 112712W2 and of 1056 (continuous filament made on 120814) were the positive controls, the negative control was a sample of plain white polyester. Results are set forth in Table 4, below.

TABLE 4

One-Hour BacTiter-Glo Assay of Fabric Samples

| | 112712W2 | MB 1066 | MB 1067 | MB 1068 | _1056 | Plain White Polyester | Media |
| --- | --- | --- | --- | --- | --- | --- | --- |
| Rep 1 | 11520 | 39006 | 29305 | 15885 | 15257 | 325805 | 416590 |
| Rep 2 | 17476 | 21982 | 18498 | 16519 | 22221 | 439072 | 395839 |
| Rep 3 | 13481 | 22873 | 15771 | 18280 | 19852 | 331968 | 380973 |
| Rep 4 | 10942 | 15845 | 12499 | 21564 | 19956 | 356658 | 395489 |
| Rep 5 | 9782 | 25992 | 19002 | 18982 | 24309 | 357103 | 372412 |
| Mean | 12640 | 25140 | 19015 | 18246 | 20319 | 362121 | 392261 |
| SEM | 1508 | 4290 | 3154 | 1121 | 1687 | 22645 | 8428 |
| Coefficient of Variation (C.V.) | 24% | 34% | 33% | 12% | 17% | 13% | 4% |
| % reduction | 97% | 94% | 95% | 95% | 95% | 8% | 0% |
| % remaining | 3% | 6% | 5% | 5% | 5% | 92% | 100% |

The MB samples of Table 4 were highly active. Notably, the variance (C.V.) of MB 1068 (which was prepared using a levigation step) was the best of all tested samples.

Example 5

Experimental data showing superior anti-microbial properties for fiber and yarn made from super pellets made in accordance with one or more systems and methods of the present invention is set forth in greater detail below. Yarn made with different heat exposures (repeated processing of filaments as described above) show statistically significant differences. It is understood that these statistically significant different exist irrespective of the selected dispersant. In the experimental data set forth below, the selected dispersant is polydimethylsiloxane (PDMS). Fiber made from such yarn is shown to exhibit enhanced anti-microbial properties.

Four identical formulations of yarn were made, and a test article (in this case, a hosiery leg) made from fiber made from the yarn was tested for anti-microbial activity. The 4 samples are described below:

Batch 1 made with no PDMS and exposed to light heat.
Batch 2 made with no PDMS and exposed to high heat.
Batch 3 made with PDMS and exposed to light heat.
Batch 4 made with PDMS and exposed to high heat.

Figure 7:
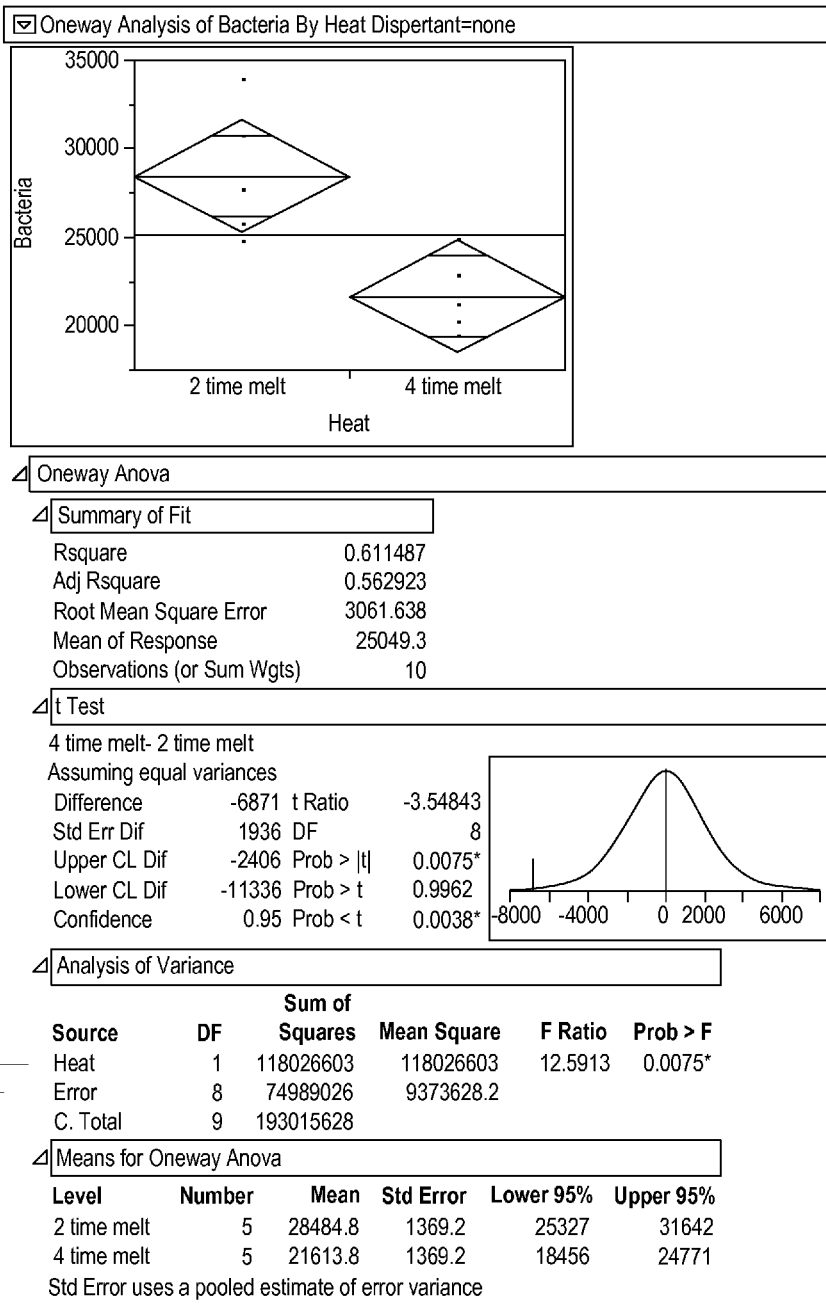
FIG. 7 is a table with graphical analysis of the heat effect without the presence of a dispersant material.
Figure 8:
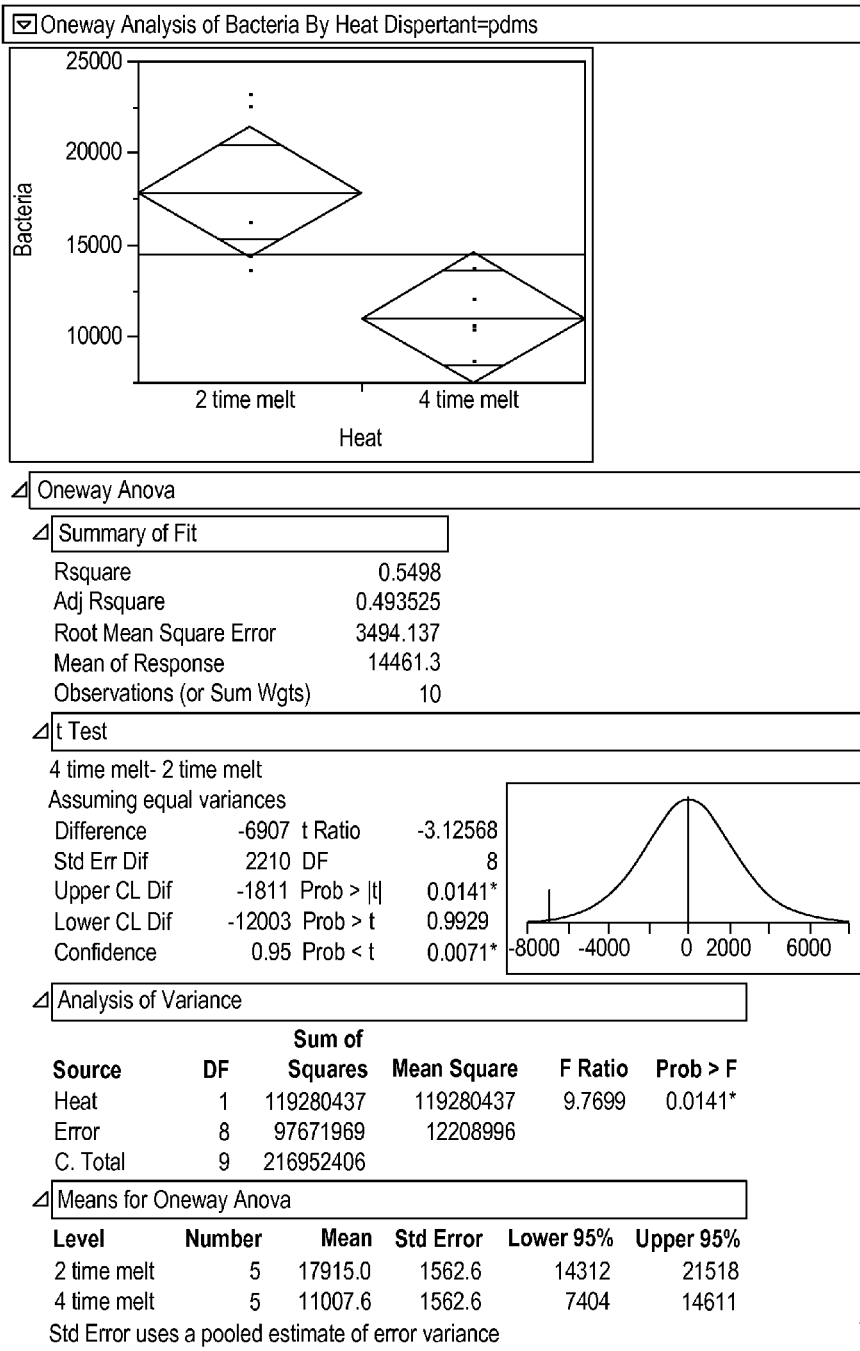
FIG. 8 is a table with graphical analysis of the heat effect with the presence of a dispersant material.

Five replicates for each above numbered batch were tested from the hosiery leg. The test bacteria used was the Gram-negative bacterium, $Escherichia$ $coli$ ($E.$ $coli$). FIG. 7 is a table with graphical analysis of the heat effect without the presence of a dispersant material, and FIG. 8 is a table with graphical analysis of the heat effect with the presence of a dispersant material.

The plots below show that there is a difference in anti-microbial activity. The high heat samples had greater activity against *E. coli* than the low heat samples regardless of whether or not a dispersant was used. The p values are significant and listed in the exhibits below in Table 5.

TABLE 5

Measured Anti-Microbial Activity of Formulations

| Replicate | Bacteria | Batch | Heat | Dispersant |
|---|---|---|---|---|
| rep1 | 24705 | 072514-1 | Low | none |
| rep2 | 30608 | 072514-1 | Low | none |
| rep3 | 27586 | 072514-1 | Low | none |
| rep4 | 25687 | 072514-1 | Low | none |
| rep5 | 33838 | 072514-1 | Low | none |
| rep1 | 20105 | 072514-2 | High | none |
| rep2 | 24783 | 072514-2 | High | none |
| rep3 | 19365 | 072514-2 | High | none |
| rep4 | 22730 | 072514-2 | High | none |
| rep5 | 21086 | 072514-2 | High | none |
| rep1 | 22426 | 072514-3 | Low | pdms |
| rep2 | 16105 | 072514-3 | Low | pdms |
| rep3 | 14352 | 072514-3 | Low | pdms |
| rep4 | 23162 | 072514-3 | Low | pdms |
| rep5 | 13530 | 072514-3 | Low | pdms |
| rep1 | 10364 | 072514-4 | High | pdms |
| rep2 | 12019 | 072514-4 | High | pdms |
| rep3 | 10500 | 072514-4 | High | pdms |
| rep4 | 13616 | 072514-4 | High | pdms |
| rep5 | 8539 | 072514-4 | High | pdms |

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method of making synthetic polymer pellet feedstock having a high concentration of an anti-microbial agent, the method comprising the steps of:

introducing a polymer into a mixing vessel, wherein the polymer is selected from the group consisting of polyester, polyethylene (PE), polypropylene (PP), polyethylene terephthalate (PET), polybutylene terephthalate (PBT), polyethylene terephthalate glycol (PETG), co-PET, polylactic acid (PLA), polytrimethylene terephthalate (PTT), rayon, nylon, nylon 6, and nylon 6,6;

introducing a polysiloxane dispersant into the mixing vessel;

introducing an anti-microbial agent comprised of a powdered metal material into the mixing vessel, the powdered metal material including:

particles of silver, in metallic or salt form, measuring between about 2 micrometers and about 12 micrometers; and particles of copper, in metallic or salt form, measuring between about 2 micrometers and about 12 micrometers;

heating and mixing the polymer, the polysiloxane dispersant and the anti-microbial agent to form a molten blend that exhibits a generally homogenous dispersal of the anti-microbial agent;

extruding the molten blend to form filaments; and cutting the filaments to form metalized synthetic polymer pellet feedstock.

2. The method of claim 1, wherein:

the particles of silver include particles of silver sulfate; and the particles of copper include copper sulfate pentahydrate.

3. The method of claim 1, wherein the particles of silver and the particles of copper each measure between about 5 micrometers and about 8 micrometers.

4. The method of claim 1, wherein the polymer includes polyethylene terephthalate (PET).

5. The method of claim 1, wherein the polymer includes polybutylene terephthalate (PBT).

6. The method of claim 1, wherein the polymer is in a powdered form.

7. The method of claim 1, wherein the polymer is in a pellet form.

8. The method of claim 1, wherein the polysiloxane dispersant is introduced to the mixing vessel at different intervals separated by at least a mixing step.

9. The method of claim 1, further comprising cooling the metalized synthetic polymer pellet feedstock by air-cooling.

10. The method of claim 1, further comprising cooling the metalized synthetic polymer pellet feedstock by water-cooling.

11. The method of claim 1, further comprising levigating the powdered metal material.

12. The method of claim 11, wherein the powdered metal material is levigated prior to introduction into the mixing vessel.

13. The method of claim 1, further comprising a re-processing step that includes:

introducing at least a portion of the metalized synthetic polymer pellet feedstock into the mixing vessel;

heating and mixing the portion of the metalized synthetic polymer pellet feedstock to form a re-processed molten blend;

extruding the re-processed molten blend to form filaments; and cutting the filaments to form re-processed metalized synthetic polymer pellet feedstock.

14. The method of claim 13, wherein the re-processing step further includes:

introducing a dye to the mixing vessel with the portion of the metalized synthetic polymer pellet feedstock; and mixing the dye and the portion of the metalized synthetic polymer pellet feedstock within the mixing vessel.

15. The method of claim 13, wherein the re-processing step further includes:

introducing an insecticide to the mixing vessel with the portion of the metalized synthetic polymer pellet feedstock; and mixing the insecticide and the portion of the metalized synthetic polymer pellet feedstock within the mixing vessel.

16. The method of claim 13, wherein the re-processing step further includes:

introducing a flame retardant to the mixing vessel with the portion of the metalized synthetic polymer pellet feedstock; and mixing the flame retardant and the portion of the metalized synthetic polymer pellet feedstock within the mixing vessel.

17. A method of making an anti-microbial yarn or fiber, the method comprising the steps of:
  (a) making metalized synthetic polymer pellet feedstock by:
    (i) introducing a first polymer into a first mixing vessel;
    (ii) introducing a dispersant into the first mixing vessel;
    (iii) introducing an anti-microbial agent comprised of a powdered metal material into the first mixing vessel, the powdered metal material including:
      particles of silver, in metallic or salt form, measuring between about 2 micrometers and about 12 micrometers; and
      particles of copper, in metallic or salt form, measuring between about 2 micrometers and about 12 micrometers;
    (iv) heating and mixing the polymer, the dispersant and the anti-microbial agent to form a first molten blend that exhibits a generally homogenous dispersal of the anti-microbial agent;
    (v) extruding the first molten blend to form filaments; and
    (vi) cutting the filaments to form the metalized synthetic polymer pellet feedstock;
  (b) introducing at least a portion of the metalized synthetic polymer pellet feedstock into a second mixing vessel;
  (c) introducing a second polymer into the second mixing vessel;
  (d) heating and mixing the portion of the metalized synthetic polymer pellet feedstock and the second polymer to form a second molten blend; and
  (e) extruding the second molten blend to form filaments usable to make an anti-microbial yarn or fiber.

18. The method of claim 17, wherein the dispersant includes a polysiloxane.

19. The method of claim 17, wherein:
the particles of silver include particles of silver sulfate; and
the particles of copper include copper sulfate pentahydrate.

20. The method of claim 17, wherein the yarn or fiber has a concentration of about 2520 ppm silver sulfate and about 318 ppm copper sulfate pentahydrate.

* * * * *